US008434493B1

(12) United States Patent
McGhie et al.

(10) Patent No.: US 8,434,493 B1
(45) Date of Patent: May 7, 2013

(54) ADJUSTABLE MOUTH SHIELD DEVICE

(76) Inventors: Eric McGhie, Charlotte, NC (US); Darrell Harvey, Charlotte, NC (US)

( * ) Notice: Subject to any disclaimer, the term of this patent is extended or adjusted under 35 U.S.C. 154(b) by 210 days.

(21) Appl. No.: 13/021,547

(22) Filed: Feb. 4, 2011

(51) Int. Cl.

| | |
|---|---|
| ***A62B 29/00*** | (2006.01) |
| ***A62B 17/04*** | (2006.01) |
| ***A62B 18/02*** | (2006.01) |
| ***A62B 18/08*** | (2006.01) |
| ***A62B 18/00*** | (2006.01) |
| ***A62B 7/00*** | (2006.01) |
| ***A62B 7/04*** | (2006.01) |
| ***A61M 15/00*** | (2006.01) |
| ***A42B 3/00*** | (2006.01) |
| ***A42B 1/06*** | (2006.01) |
| ***H04R 25/00*** | (2006.01) |
| ***H04R 1/20*** | (2006.01) |

(52) U.S. Cl.

USPC ................. 128/863; 128/200.28; 128/201.22; 128/201.18; 128/201.19; 128/200.27; 128/204.18; 128/207.17; 128/207.18; 128/201.24; 128/200.24; 128/205.11; 128/204.29; 128/202.26; 128/204.22; 128/207.11; 128/205.26; 2/6; 2/209; 381/338; 381/380; 381/371; 381/374; 381/375; 381/376; 381/377; 381/378; 381/379; 381/381; 381/382; 181/20; 181/21; 181/22; 181/129; 181/130; 181/135

(58) Field of Classification Search ............. 128/200.28, 128/201.22, 201.18, 201.19, 200.27, 204.18, 128/207.17, 207.18, 201.24, 200.24, 205.11, 128/204.29, 202.26, 204.22, 207.11, 205.26; 2/6, 209; 381/371, 374–382, 338; 181/20–22, 181/129, 130, 135

See application file for complete search history.

(56) References Cited

U.S. PATENT DOCUMENTS

| | | | | |
|---|---|---|---|---|
| 3,850,168 | A | 11/1974 | Ferguson et al. | |
| 5,717,991 | A | 2/1998 | Nozaki et al. | |
| 6,595,207 | B1 | 7/2003 | McDonald | |
| 6,619,288 | B2 | 9/2003 | Demers et al. | |
| 6,920,228 | B2 * | 7/2005 | Redmer et al. ................ | 381/370 |
| 2002/0131616 | A1 * | 9/2002 | Bronnikov et al. ........... | 381/370 |

* cited by examiner

*Primary Examiner* — Patricia Bianco
*Assistant Examiner* — Nihir Patel

(57) ABSTRACT

The adjustable mouth shield device provides an adjustably fitted mouth shield with adjustable headband for secure fit. The adjustable headband is fastened to the padded earpiece. The straight first extension from the earpiece is angled downwardly and forwardly to terminate in a swivel joint providing almost 360 degrees of swivel. The second extension is arced both downwardly and forwardly. The u-shaped mouthpiece is fitted to the adjustable spring mount for horizontal pivot of the mouthpiece. The mouthpiece may, by virtue of the swivel joint and the spring mount, be moved completely away from a user's mouth and, in turn, pivoted and swiveled to be directly in front of the user's mouth. The inward curves at the distal end of the mouthpiece aid in sliding on the disposable pads that shield a user from objects, foods and other materials.

13 Claims, 3 Drawing Sheets

ADJUSTABLE MOUTH SHIELD DEVICE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

There are often times and professions that call for an individual's breath to be shielded from work objects and the like. This may be especially true in food preparation and food service industries. The present device provides unique advantages in the art.

FIELD OF THE INVENTION

The adjustable mouth shield device relates to mouth guards and more especially to a mouth shield device with adjustable headband, an earpiece, and a mouthpiece with disposable pad affixed to the earpiece via extensions with a swivel joint.

SUMMARY OF THE INVENTION

The general purpose of the adjustable mouth shield device, described subsequently in greater detail, is to provide an adjustable mouth shield device which has many novel features that result in an improved adjustable mouth shield device which is not anticipated, rendered obvious, suggested, or even implied by prior art, either alone or in combination thereof.

To attain this, the adjustable mouth shield device provides an adjustably fitted mouth shield with adjustable headband for secure fit. The adjustable headband is fastened to the earpiece that may include a curvature of 180 degrees and more and may also include a pad. The earpiece may have a straight first extension angled downwardly and forwardly to terminate in a swivel joint. The swivel joint may provide almost 360 degrees of swivel. A more basic embodiment of the device may exclude the swivel joint. The second extension may be arced, both downwardly and forwardly. The u-shaped mouthpiece fitted to the second extension may be fitted directly or may be fitted by a spring mount that allows horizontal pivot of the mouthpiece. The spring mount may be provided with an adjustment that may be relaxed to provide movable mouthpiece placement or may be adjusted to provide that the mouthpiece returns to a position in front of a user's mouth. The mouthpiece may, by virtue of the swivel joint and the spring mount, be moved completely away from a user's mouth and, in turn, pivoted and swiveled to be directly in front of the user's mouth. The u-shaped mouthpiece may include a pair of inward curves at the distal end to aid in sliding on the disposable pads. The pads may include bactericidal and fungicidal properties and may also be provided in elasticized materials.

The device is useful in many pursuits but is especially useful in the food industries to confine breathing, coughing and the like to the user and not allow such to invade food items.

The device displays a restaurant's concern for customer safety, well-being, and satisfaction. Adjustability ensures that the device may fit any user. The device is made of lightweight materials and is easily applied and removed.

Thus has been broadly outlined the more important features of the improved adjustable mouth shield device so that the detailed description thereof that follows may be better understood and in order that the present contribution to the art may be better appreciated.

An object of the adjustable mouth shield device is to shield a user's breath from a given area, object, person, or foodstuff.

Another object of the adjustable mouth shield device is to adjustably fit a user's head.

A further object of the adjustable mouth shield device is to provide a padded earpiece for further secure fit.

An added object of the adjustable mouth shield device is to provide a mouthpiece with removable, disposable pads.

And, an object of the adjustable mouth shield device is to provide a spring mount for the mouthpiece.

Still another object of the adjustable mouth shield device is to provide for selectively pivoting the mouthpiece away from and in front of a user's mouth.

These together with additional objects, features and advantages of the improved adjustable mouth shield device will be readily apparent to those of ordinary skill in the art upon reading the following detailed description of presently preferred, but nonetheless illustrative, embodiments of the improved adjustable mouth shield device when taken in conjunction with the accompanying drawings.

DETAILED DESCRIPTION OF THE DRAWINGS

With reference now to the drawings, and in particular FIGS. 1 through 5 thereof, the principles and concepts of the adjustable mouth shield device generally designated by the reference number 10 will be described.

Figure 1:
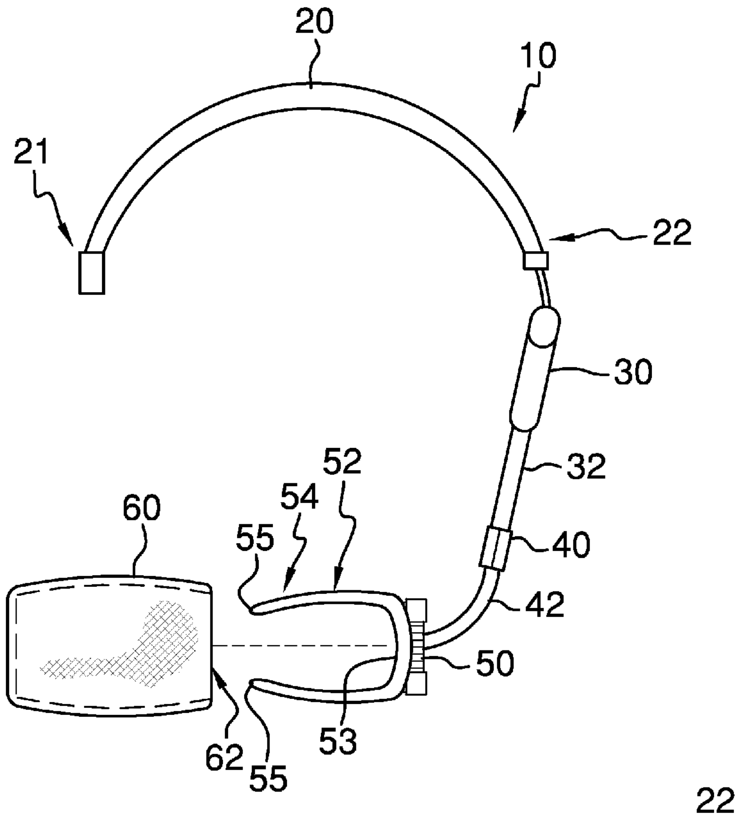
FIG. 1 is a frontal elevation view.

Referring to FIG. 1, the device 10 partially comprises the adjustable headband 20 having a first side 21 spaced apart from the second side 22.

Figure 5:
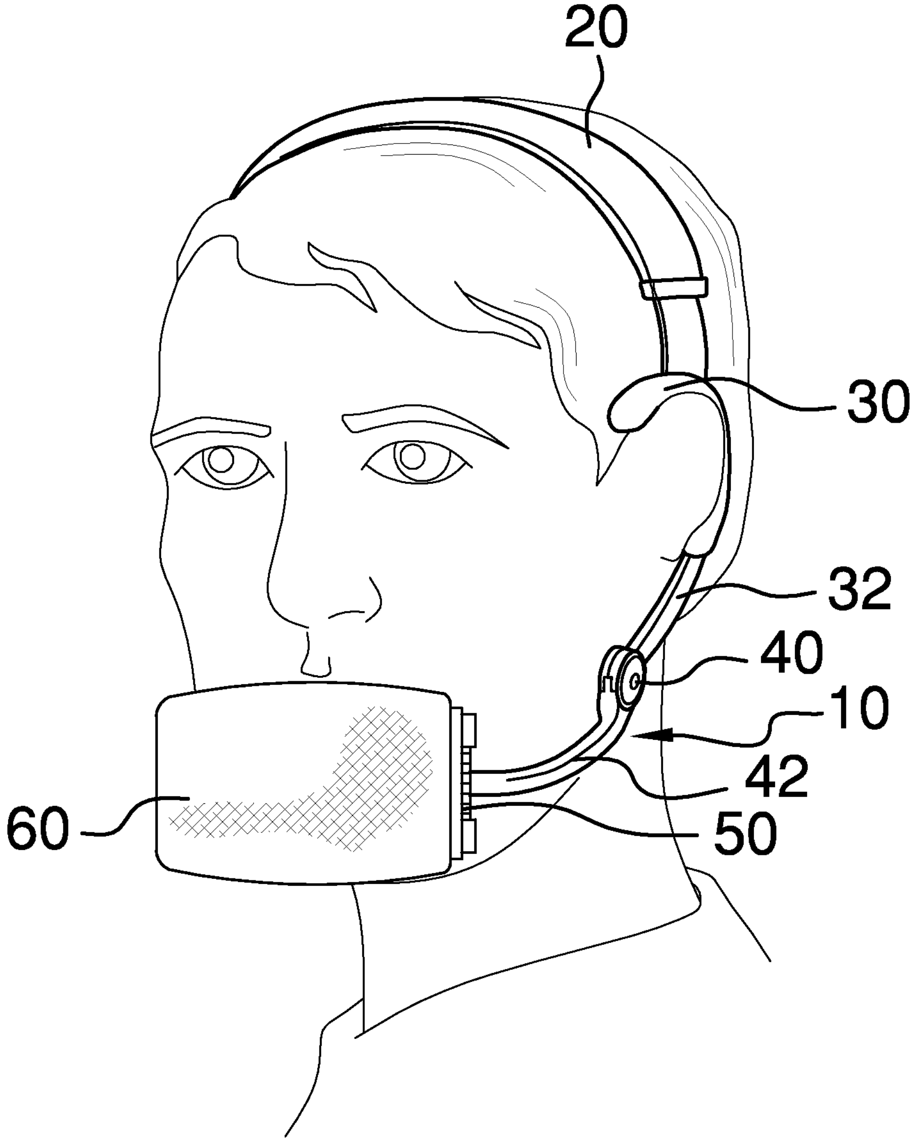
FIG. 5 is an in use view.

Referring to FIG. 5, the adjustable headband 20 is removably fitted atop a user's head.

Figure 3:
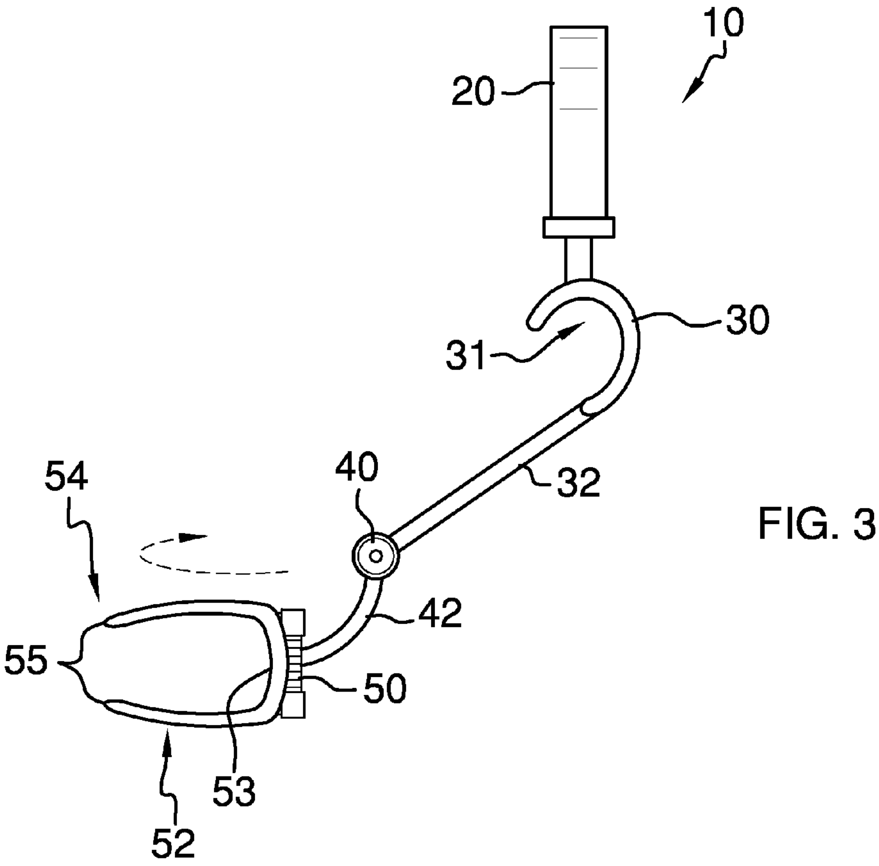
FIG. 3 is a lateral elevation view illustrating pivot capability of the mouthpiece at the spring mount.
Figure 4:
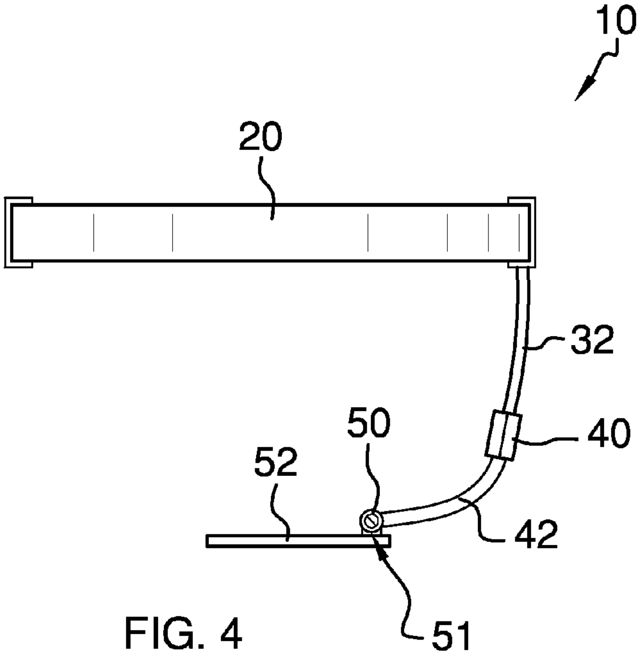
FIG. 4 is a top plan view.

Referring to FIG. 3, the padded earpiece 30 is affixed downwardly to the adjustable headband 20 second side 22. The earpiece 30 has at least a 180 degree curvature 31. The first extension 32 is extended straight, forwardly and downwardly from the earpiece 30.

Figure 2:
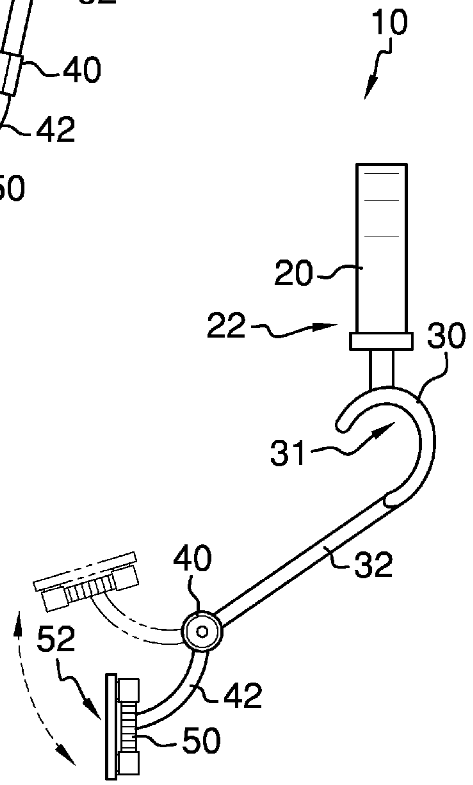
FIG. 2 is a lateral elevation view illustrating swivel of the second extension at the swivel joint.

Referring to FIG. 2, the swivel joint 40 is affixed distally to the first extension 32. The swivel joint 40 provides for almost 360 degrees of swivel.

Referring to FIG. 4 and again to FIG. 1, an arced second extension 42 extends downwardly and forwardly from the swivel joint 40.

Referring again to FIG. 3 and FIG. 4, the spring mount 50 is affixed vertically to the second extension 42. The spring mount 50 provides a flexible attachment for the u-shaped mouthpiece 52. The spring mount 50 further provides pivotal attachment to the u-shaped mouthpiece 52 whereby the mouthpiece 52 may be pivoted away from a user's mouth.

Referring to FIG. 2 and FIG. 3, the swivel joint 40 allows a user to pivot the mouthpiece 52 upwardly and downwardly and even backwardly. The spring mount 50 allows a user to pivot the mouthpiece 52 toward and away from a user's mouth.

Referring again to FIG. 1, the u-shaped mouthpiece 52 has a base 53 spaced apart from a distal end 54. The base 53 is affixed vertically to the spring mount 50. An adjustment 51 is disposed upwardly in the spring mount 50.

Referring to FIG. 3, the mouthpiece 52 may be positioned to be in front of a user's mouth, and the adjustment 51 is then tightened such that any movement of the mouthpiece 52 sees the mouthpiece 52 automatically return to a position in front of the user's mouth. The adjustment 51 may be relaxed so that the mouthpiece 52 may be positioned as chosen. The pair of mirror image inward curves 55 is disposed on the distal end 54.

Referring to FIG. 1, the inward curves 55 importantly aid in the installation of pads 60. A plurality of disposable pads 60 is provided. Each pad 60 has an open end 62, whereby each pad 60 is removably fitted over the u-shaped mouthpiece 52. The pads 60 are supplied to fit snugly over the u-shaped mouthpiece 52. The pads 60 are bactericidal and fungicidal. The pads 60 are also provided in elastic materials for even better fit over the u-shaped mouthpiece 52.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the adjustable mouth shield device may be used.

What is claimed is:

1. An adjustable mouth shield device comprising:

an adjustable headband having a first side spaced apart from a second side, the adjustable headband removably fitted atop a user's head;

a earpiece affixed downwardly to the adjustable headband second side, the earpiece having at least a 180 degree curvature;

a first extension extended straight, forwardly and downwardly from the earpiece;

an arced second extension extended downwardly and forwardly from the first extension;

a u-shaped mouthpiece having a base spaced apart from a distal end, the base affixed vertically to the second extension;

a plurality of disposable pads, each pad having an open end;

whereby each pad is removably fitted over the u-shaped mouthpiece; and wherein the u-shaped mouthpiece further comprises a pair of mirror image inward curves disposed on the distal end.

2. The device according to claim 1 wherein the earpiece is further padded.

3. The device according to claim 2 further comprising a spring mount affixed vertically to the second extension;

the u-shaped mouthpiece fitted to the spring mount.

4. The device according to claim 3 wherein the pads are further bactericidal and fungicidal.

5. The device according to claim 2 wherein the pads are further bactericidal and fungicidal.

6. The device according to claim 1 further comprising a spring mount affixed vertically to the second extension;

the u-shaped mouthpiece fitted to the spring mount.

7. The device according to claim 6 wherein the pads are further bactericidal and fungicidal.

8. The device according to claim 1 wherein the pads are further bactericidal and fungicidal.

9. An adjustable mouth shield device comprising:

an adjustable headband having a first side spaced apart from a second side, the adiustable headband removably fitted atop a user's head;

a earpiece affixed downwardly to the adjustable headband second side, the earpiece having at least a 180 degree curvature;

a first extension extended straight, forwardly and downwardly from the earpiece;

an arced second extension extended downwardly and forwardly from the first extension;

a u-shaped mouthpiece having a base spaced apart from a distal end, the base affixed vertically to the second extension;

a plurality of disposable pads, each pad having an open end;

whereby each pad is removably fitted over the u-shaped mouthpiece; and a spring mount affixed vertically to the second extension;

the u-shaped mouthpiece fitted to the spring mount.

10. The device according to claim 9 wherein the earpiece is further padded.

11. The device according to claim 10 wherein the pads are further bactericidal and fungicidal.

12. The device according to claim 9 wherein the pads are further bactericidal and fungicidal.

13. An adjustable mouth shield device comprising, in combination:

an adjustable headband having a first side spaced apart from a second side, the adjustable headband removably fitted atop a user's head;

a padded earpiece affixed downwardly to the adjustable headband second side, the earpiece having at least a 180 degree curvature;

a first extension extended straight, forwardly and downwardly from the earpiece;

a swivel joint affixed distally to the first extension;

an arced second extension extended downwardly and forwardly from the swivel joint;

a spring mount affixed vertically to the second extension;

an adjustment disposed upwardly in the spring mount;

a u-shaped mouthpiece having a base spaced apart from a distal end, the base affixed vertically to the spring mount;

a pair of mirror image inward curves disposed on the distal end;

a plurality of disposable pads, each pad having an open end;

whereby each pad is removably fitted over the u-shaped mouthpiece.

* * * * *